United States Patent
Inoue

[19]

[11] Patent Number: 5,889,210
[45] Date of Patent: Mar. 30, 1999

[54] APPARATUS FOR DETECTING SEMICONDUCTOR BONDING DEFECTS

[75] Inventor: Yoshikazu Inoue, Kitakyushu, Japan

[73] Assignee: Kyushu Electronics Systems, Inc., Fukuoka-ken, Japan

[21] Appl. No.: 914,724

[22] Filed: Aug. 19, 1997

[30] Foreign Application Priority Data

Aug. 30, 1996 [JP] Japan .................................... 8-230484

[51] Int. Cl.$^6$ ................................................. G01N 29/08
[52] U.S. Cl. .................................. 73/588; 73/827; 73/842
[58] Field of Search .............................. 73/588, 618, 801, 73/827, 842

[56] References Cited

U.S. PATENT DOCUMENTS

| | | | |
|---|---|---|---|
| 4,184,373 | 1/1980 | Evans et al. | 73/588 |
| 4,366,713 | 1/1983 | Gilmore et al. | 73/618 |
| 5,372,042 | 12/1994 | Jarman et al. | 73/588 |
| 5,481,917 | 1/1996 | Arima et al. | 73/618 |
| 5,513,531 | 5/1996 | Sapia et al. | 73/618 |

*Primary Examiner*—George Dombroske
*Assistant Examiner*—Max H. Noori
*Attorney, Agent, or Firm*—Jordan and Hamburg LLP

[57] ABSTRACT

A bonding defect detecting apparatus is provided for operation in conjunction with an ultrasonic wire bonder using an ultrasonic oscillator driven by a signal. The apparatus has A/D converters for digitally converting a signal waveform of the signal by real-time sampling during a bonding operation. A digital signal processing device is provided for calculating at least one signal characteristic of each of the signal waveforms for each of a plurality of the bonding operation. A data accumulating devices accumulates the at least one signal characteristic for n number of bonding operations of the plurality of the bonding operation. A calculating device calculates an average signal characteristic of the signal characteristics of the n number of bonding operations. And a comparing device compares the average signal characteristic with a corresponding present signal characteristic of a last bonding operation of the plurality of the bonding operation, occurring after the n number of bonding operations, to thereby determine whether a bonding defect exists. Preferably, the n number of bonding operations are a most recent n number of bonding operations occurring before the last bonding operation. In an embodiment, the signal waveform includes both a voltage waveform and a current waveform from which signal characteristics such as average voltage, average current, peak voltage, peak current, a phase difference between the voltage waveform and a current waveform and an impedance are determined.

34 Claims, 7 Drawing Sheets method of determining
voltage average value method of determining
current average value method of determining
voltage frequency method of determining
current frequency method of determining phase difference method of determining phase difference

APPARATUS FOR DETECTING SEMICONDUCTOR BONDING DEFECTS

BACKGROUND OF THE INVENTION

The present invention relates to an apparatus for detecting bonding defects of a semiconductor element such as an IC by monitoring an output waveform of an ultrasonic oscillator of a bonder.

In the case of a semiconductor element having as many as several hundreds of pins, it is usual to determine the quality of the products by bonding the pins using ultrasonic waves and then measuring the characteristic of the product with a semiconductor tester. However, with this method, even when bonding strength does not satisfy rated value, if the pins are only electrically connected, no bonding defect will be detected, and there is a high possibility that several bonding defects may appear after the product has been shipped.

Further, although there is conventionally a bonding defect detecting apparatus aiming at the variations of voltage waveform and current waveform of an ultrasonic oscillator of a bonder, the measuring method is based on the measurement of absolute values. That is, the apparatus is used to measure the effective values of the voltage and current during the bonding operation, setting a reference value based on the average value thereof, and determining whether or not the product is qualified by setting this reference value to be a fixed value.

However, in the case of an actual bonding for an IC, there are differences in reference values resulting from different types of apparatuses or semiconductor elements, or there are differences in average value due to positions of the pins on the frame. Therefore, using the reference value as a fixed value is not practical because of gross errors produced when determination is made.

Further, even in the case of the same semiconductor element, effective values of voltage and current fluctuate with time due to wear, and a rise in temperature, of the tool at a top end of the bonder, and the conventional apparatus using average values has a problem of being unable to cope with the fluctuation, with the result that the criterion of determination of the quality of the product is not kept constant.

SUMMARY OF THE INVENTION

The present invention has been made to solve the above-mentioned problems, and its object is to provide a bonding defect detecting apparatus that enables bonding defects to be detected irrespective of a difference in type and position of a pin, without being influenced by an operation state of the bonder.

To attain the above-described object, according to the present invention, there is provided a semiconductor bonding defect detecting apparatus which is connected to a wire bonder for performing bonding of pins by use of ultrasonic waves generated from an ultrasonic oscillator and which comprises means for performing an analog-digital conversion of a voltage waveform and current waveform of the ultrasonic oscillator that are input thereto by being sampled on a real time basis from the ultrasonic oscillator during a bonding process, digital signal processing means for calculating specific data such as frequency, phase difference between the voltage waveform and the current waveform and impedance from the sampled data of the voltage waveform and current waveform that are digitally converted, data accumulating means for accumulating a digital data that has been calculated by the digital signal processing means for each pin, and determining means for comparing a previous average value of a plurality of digital data items that are accumulated in the data accumulating means with a present digital data item that is obtained by the operation of the digital signal processing means to thereby determine a bonding defect.

The previous average value of the plurality of digital data items in the determining means is calculated using a plurality of the most recent data items.

DETAILED DESCRIPTION OF THE INVENTION

Figure 1:
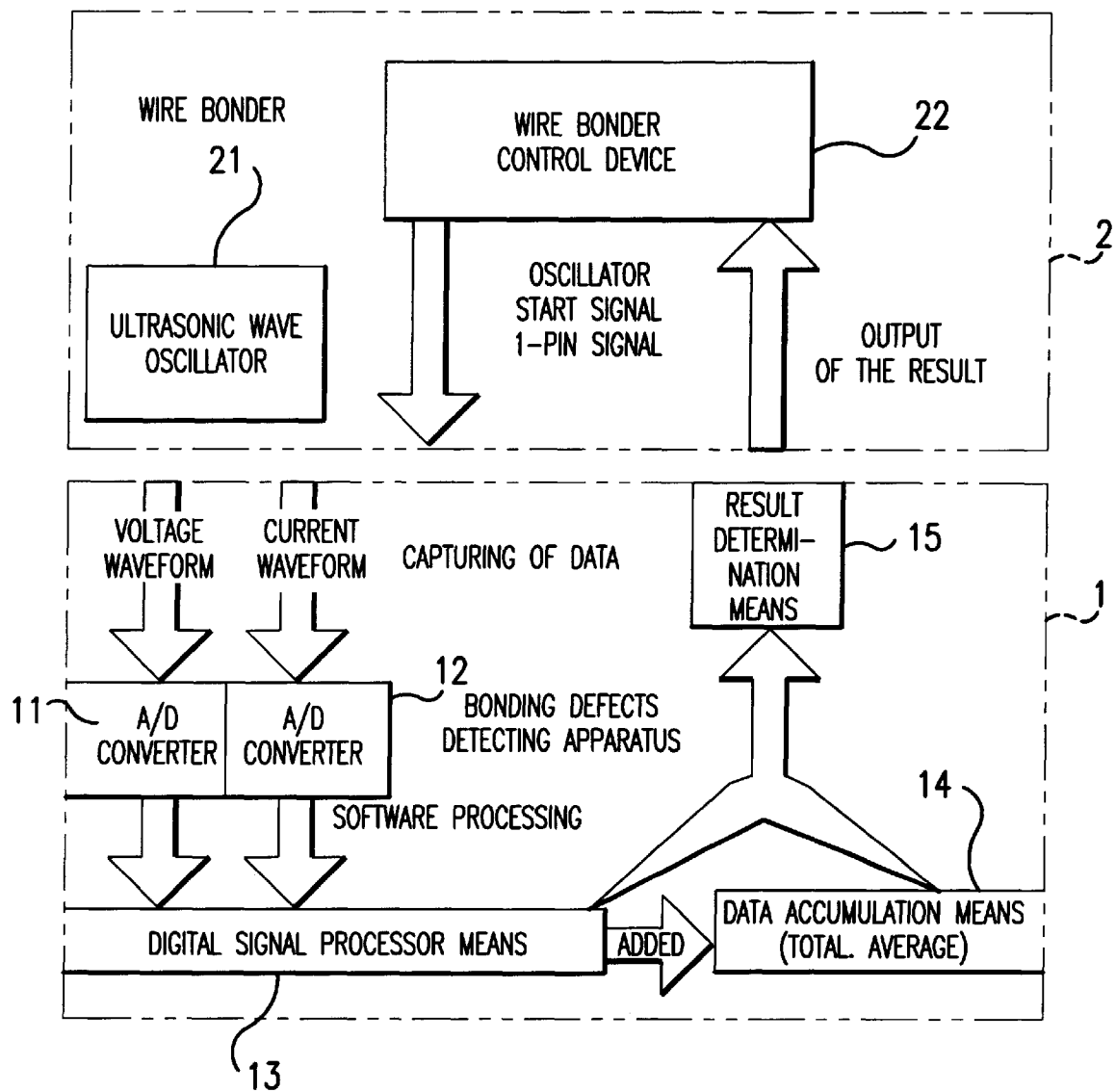
FIG. 1 is a block diagram illustrating a structure of a bonding defects detecting apparatus according to the present invention.

FIG. 1 is a block diagram illustrating the structure of a bonding defect detecting apparatus according to the present invention. This bonding defect detecting apparatus 1 is connected to a wire bonder 2 when it is in use. The wire bonder 2 is composed of an ultrasonic oscillator 21 and a wire bonder control device 22. The bonding defect detecting apparatus is equipped with A/D converters 11, 12 which receive a voltage waveform and a current waveform generated from the ultrasonic oscillator 21 to thereby perform a digital conversion, digital signal processing means 13 for calculating a frequency, a phase difference between the voltage waveform and the current waveform and impedance from sampled data of the voltage waveform and current waveform that are digitally converted, data accumulating means 14 for accumulating digital data calculated by the digital signal processing means for each pin, and determining means 15 for comparing a previous average value of a plurality of digital data items accumulated in the data accumulating means 14 with a present digital data item calculated by the digital signal processing means 13 to thereby determine a bonding defect. It is to be noted that operation of the digital signal processing means 13 is performed through software processing that is executed by a high speed DSP (Digital Signal Processor).

Figure 2:
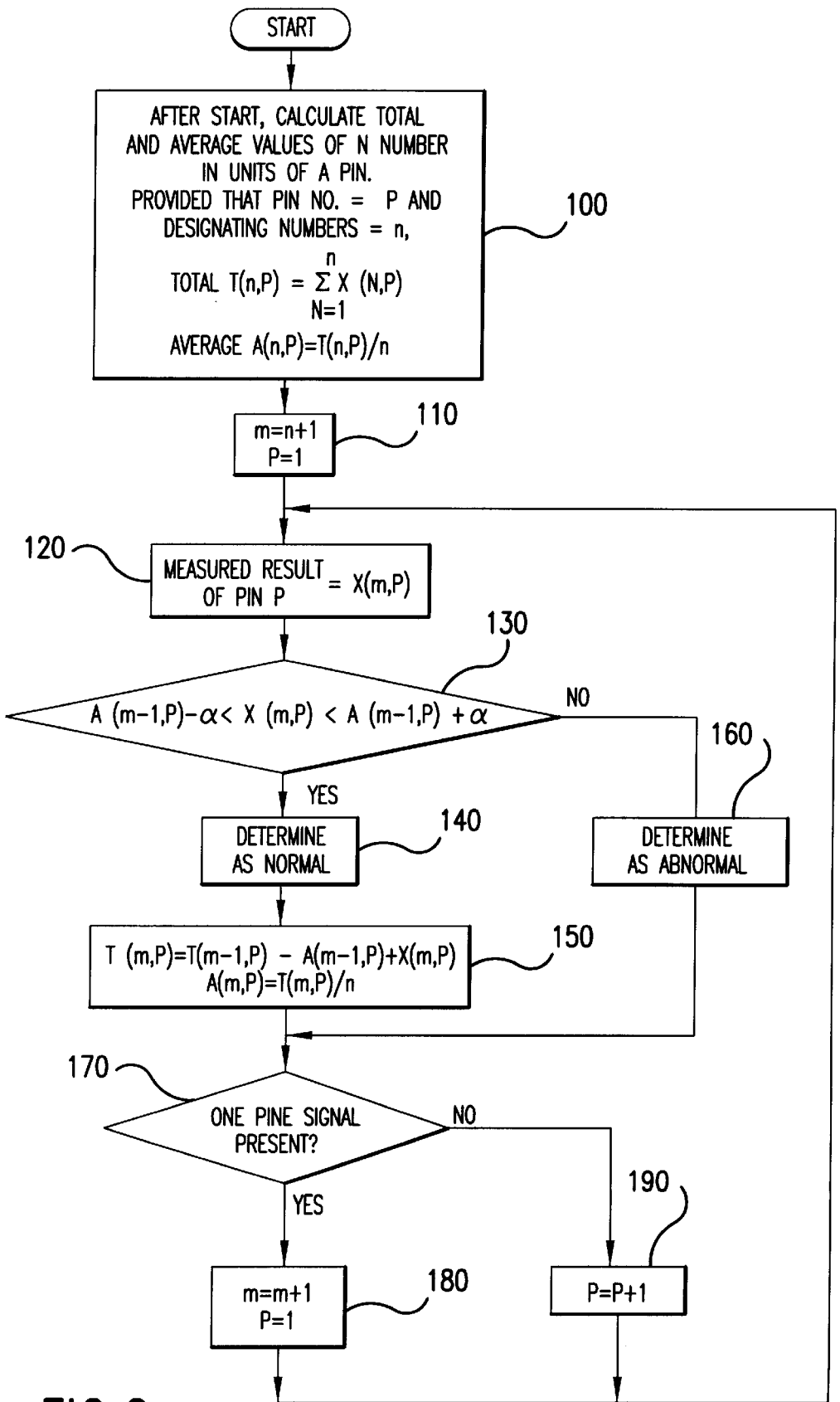
FIG. 2 is a flow chart illustrating a method of averaging data according to the present invention.
Figure 3A:
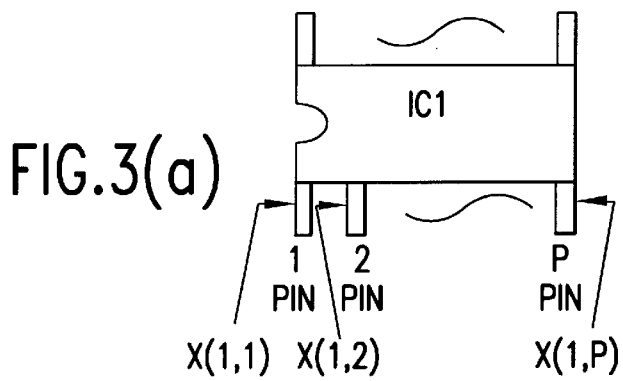
FIG. 3($a$) through 3($d$) are illustrations of numbers of pins IC1 to ICm, respectively.
Figure 3B:
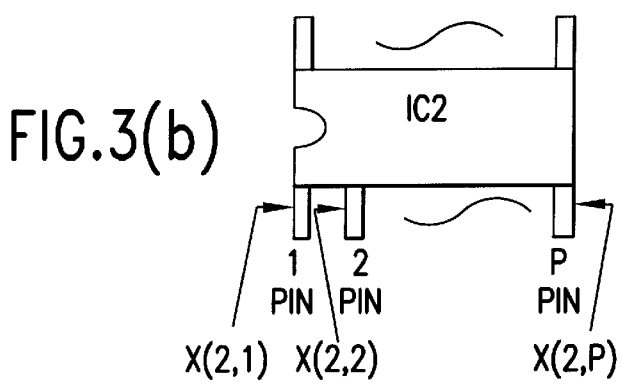
Figure 3C:
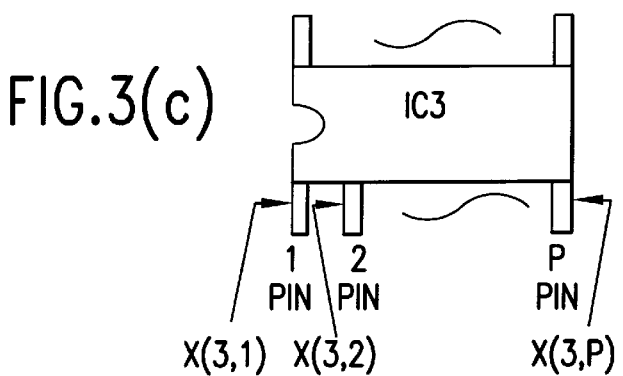
Figure 3D:
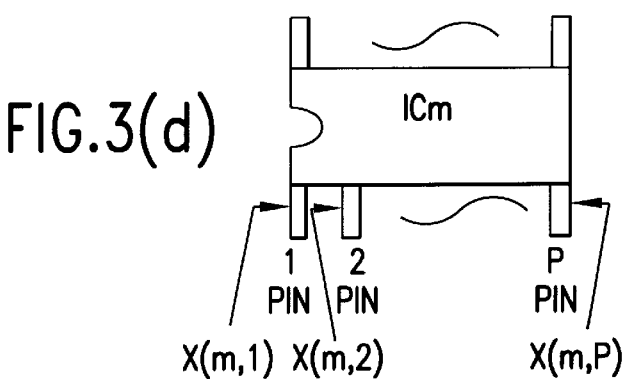

Next, the data averaging method in the data accumulating means 14 will be explained with reference to an illustrative view of the pin numbers of IC1 to ICm shown in FIG. 3 as well as a flow chart shown in FIG. 2.

Assuming that the number of pins to be averaged is represented by n and the pin number is represented by P, the total (n, P) of an n-number measured values of pins P that run from the measured value X (I, P) to the measured value X (n, P) regarding an n-number of pins is expressed by the following equation [1].

$$T(n, P) = \sum_{N=1}^{n} P(N, P) \qquad \text{[Equation 1]}$$

In this case, the average value A (n, P) is expressed as follows.

$$A(n, P) = T(n, P)/n \text{ (FIG. 2, step 100)}.$$

From the (n+1)th pin, the data is processed at a high speed in the following way.

Assume that measurement has been performed of the mth (m>n) order pin (step 110).

Assume that the measured value of the pin P be X (m, P) (step 120). Confirm whether or not this measured value satisfies the following formula (step 130).

$$A(m-1, P) - \alpha < X(m, P) < A(m-1, P) + \alpha$$

If the measured value satisfies, it is determined that the pin is normal (qualified) (step 140).

When the pin is normal, the average value of an n number of the most recent measured values is calculated as follows.

The total T (m, P) of an n number of pins P measured values of (m−n+1) number that cover from the measured value X (m−n+1, P) to the measured value X (m, P) is expressed as follows.

$$T(m,P) = T(m-1, P) - A(m-1, P) + X(m, P)$$

In this case, the average value A (m, P) is expressed as follows.

$$A(m, P) = T(m, P)/n \text{ (step 150)}.$$

Unless the requirement of step 130 is satisfied, it will be determined that the product is abnormal (unqualified) (step 160).

It is then determined whether or not the IC to be measured next will be a new IC (step 170).

If this IC is new, +1 is added to the IC number, whereby the pin number is set to be 1 (step 180).

If it is not a new IC, +1 is added to the pin number (step 190).

The averaging operation is repeated from step 120.

(Embodiment)

Figure 4A:
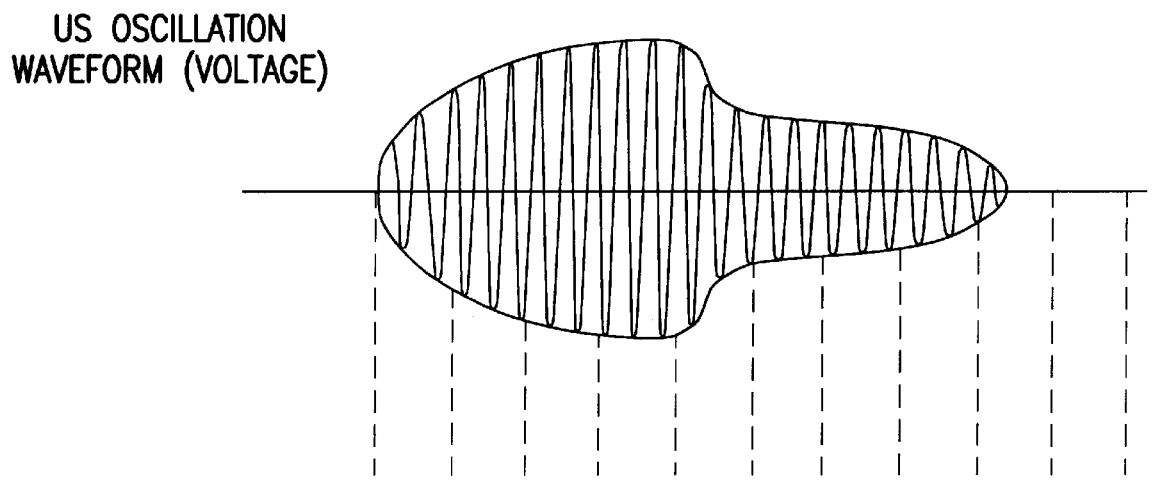
FIG. 4 shows are an output voltage waveform diagram (a) and an output current waveform diagram (b) respectively, of an ultrasonic oscillator during a bonding operation.
Figure 4B:
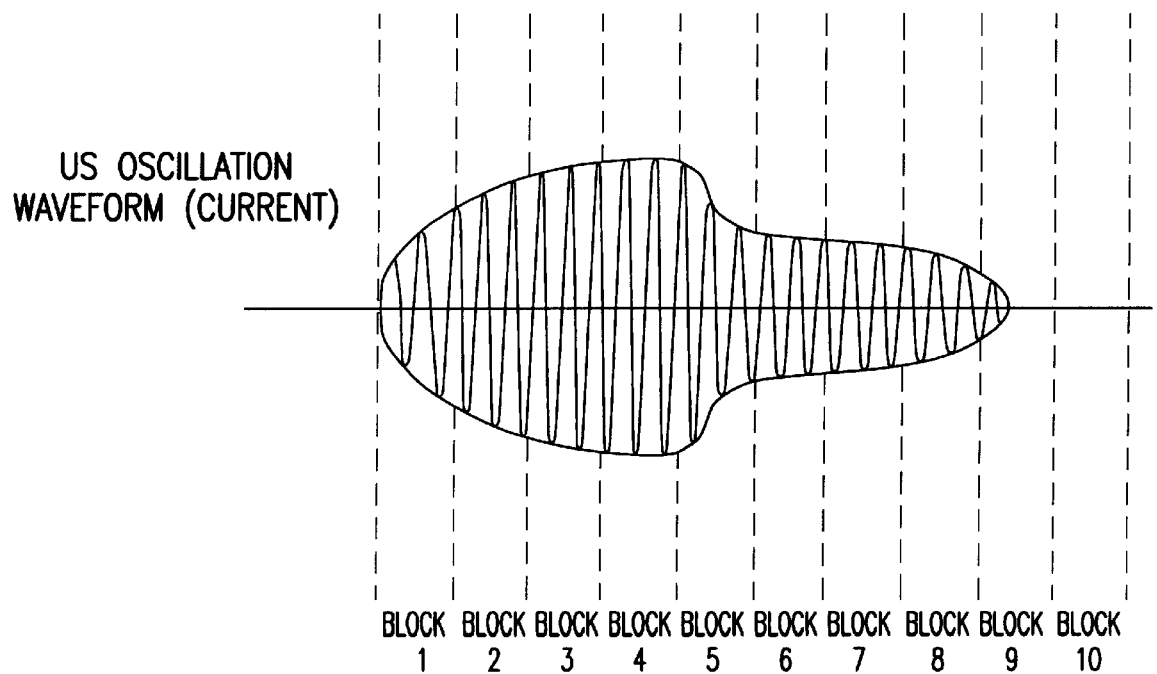

FIG. 4 shows illustrate typical examples of an output waveform (a) from the ultrasonic oscillator at the time of bonding a single pin a current waveform (b). The envelope curve of the waveforms exhibits a specific curvilinear configuration as illustrated. The fact that the amplitude of the waveforms (a) and (b) becomes small midway in the contour thereof is considered to indicate that at a point in time when the bonding processes complete the welding of the pin, the voltage drop between the contact points lessens. When the welding is defective, the envelope curves of the waveforms (a) and (b) does not become a typical pattern as shown in FIG. 4 but becomes a distorted pattern. The waveforms (a) and (b) thus divided into, for example, 10 blocks and the data is measured for each block.

Figure 5:
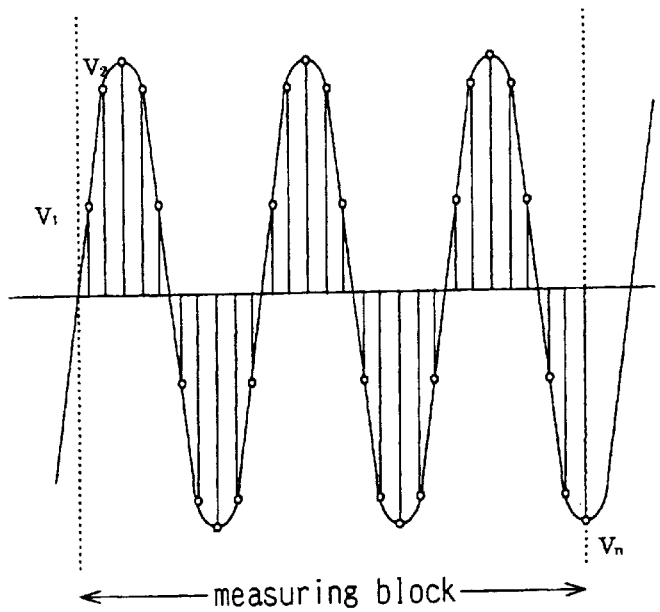
FIG. 5 is an illustration of how to obtain an average voltage value.

FIG. 5 illustrates a method of determining an average voltage value within a region of a measuring block. The measuring block is divided into an n-number of parts, thereby performing sampling of the voltage waveform. And, the average voltage value $V_{AVE}$ is determined using the respective sampled values $V_i$.

$$V_{AVE} = \left\{ \sum_{i=1}^{n} |V_i| \right\} / n \qquad \text{[Equation 2]}$$

Also, the maximum value of the voltage is determined from a maximum value among $|V_1|$ to $|V_n|$.

Figure 6:
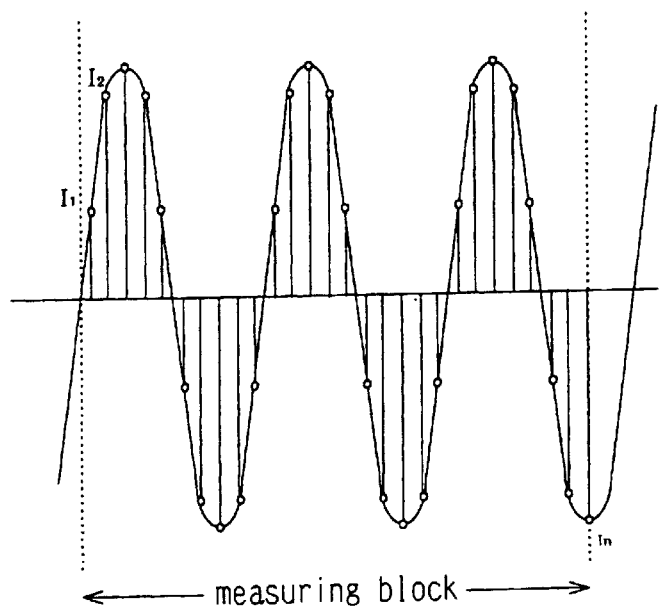
FIG. 6 is an illustration of how to obtain an average current value.

FIG. 6 illustrates a method of determining an average current value within the region of a measuring block. The measuring block is divided into an n number of parts, thereby performing sampling of the current waveform. And, the average current value $I_{AVE}$ is determined using the respective sampled values $I_i$.

$$I_{AVE} = \left\{ \sum_{i=1}^{n} |I_i| \right\} / n \qquad \text{[Equation 3]}$$

Also, the maximum value of the current is determined from a maximum value among $|I_1|$ to $|1_n|$.

An impedance Imp is determined using the average voltage value $V_{AVE}$ and the average value current $I_{AVE}$.

$$Imp = V_{AVE}/I_{AVE}$$

Figure 7:
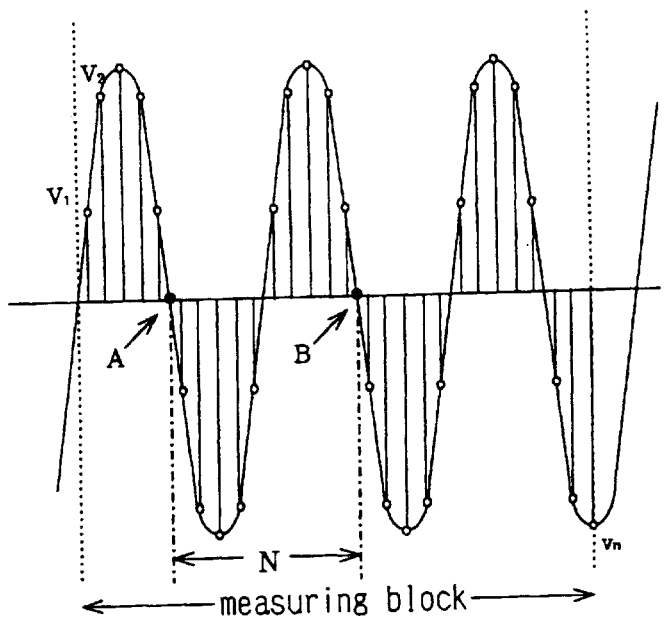
FIG. 7 is an illustration of how to obtain a voltage frequency.

FIG. 7 illustrates a method of determining a voltage frequency. The voltage frequency $V_f$ is expressed by the equation:

$$V_f = f_s/N$$

Wherein, $f_s$ represents the sampling frequency. N represents the number of data items that corresponds to one cyclic period and, in this case, the number of data items that corresponds to one cyclic period is determined from the number of samplings that falls within one cyclic period from a zero-cross point A to a zero-cross point B.

Figure 8:
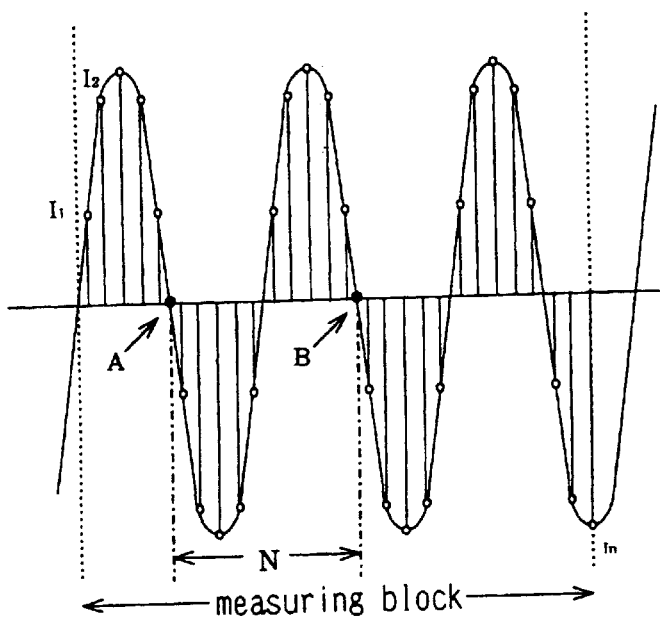
FIG. 8 is an illustration of how to obtain a current frequency.

FIG. 8 illustrates a method of determining a current frequency. The current frequency $I_f$ is expressed by the equation:

$$I_f = f_s/N$$

Wherein, $f_s$ represents the sampling frequency. N represents the number of data items that corresponds to one cyclic period and, in this case, the number of data items that corresponds to one cyclic period is determined from the number of samplings that falls within one cyclic period from a zero-cross point A to a zero-cross point B.

Figure 9:
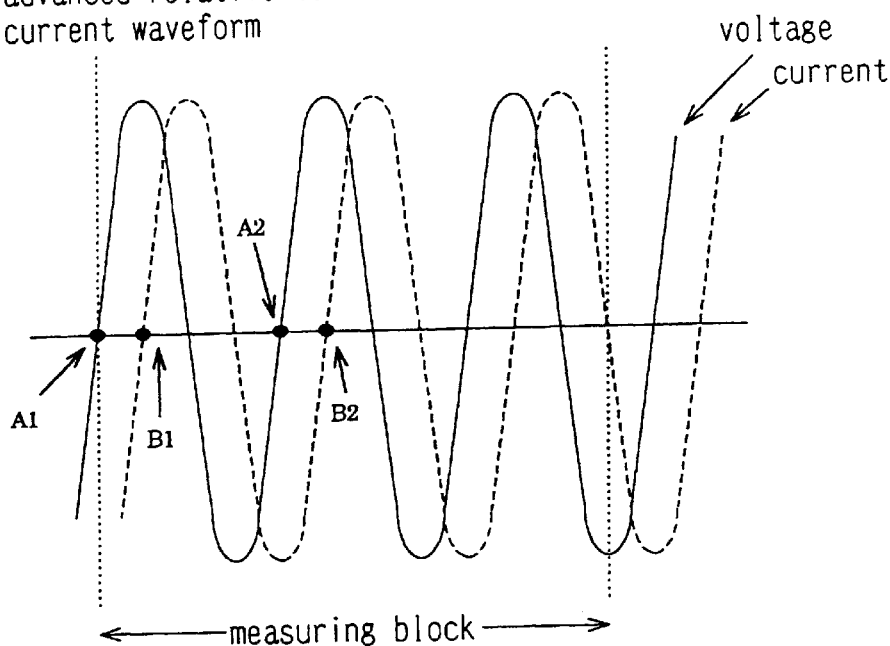
FIG. 9 is an illustration of how to obtain a phase difference when a voltage waveform is advanced relative to a current waveform.
Figure 10:
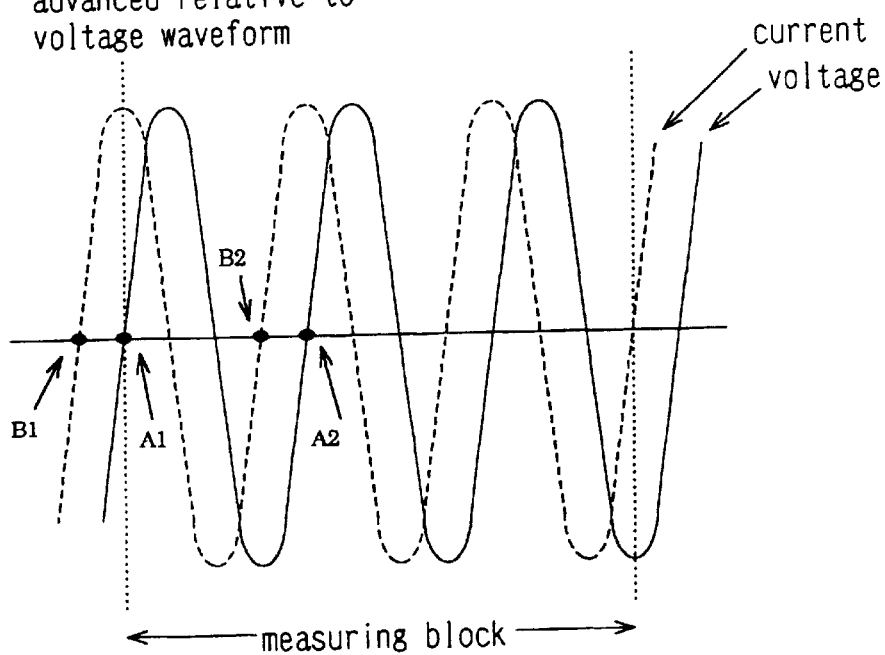
FIG. 10 is an illustration of how to obtain a phase difference when the current waveform is advanced relative to the voltage waveform.

FIGS. 9 and 10 are diagrams illustrating a method of determining a phase difference, with FIG. 9 illustrating a case where the voltage waveform is advanced relative to the current waveform and FIG. 10 illustrating a case where the current waveform is advanced relative to the voltage waveform. In FIG. 9, determination is performed on the zero-cross points A1 and A2 of the voltage waveform and the zero-cross points B1 and B2 of the current waveform and then an operation is performed on the phase difference of the (B1−A1) by using the following equation.

$$\text{Phase Difference} = \{(B1-A1) \times 360°\}/(B2-B1)$$

It is to be noted that when the phase difference is more than 360°, a value that has been obtained by subtracting 360° therefrom is set to be the phase difference.

Also, FIG. 10 illustrates a case where the current waveform is advanced relative to the voltage waveform, and determination is performed of the zero-cross points A1 and A2 of the voltage waveform and the zero-cross points B1 and B2 of the current waveform. An operation is then performed on the phase difference of the (B2–A1) by using the following equation.

$$\text{Phase Difference} = \{(B2-A1) \times 360°\}/(B2-B1)$$

It is to be noted that when the phase difference is more than 360°, a value that has been obtained by subtracting 360° therefrom is set to be the phase difference.

If there exists an abnormality in the voltage waveform or current waveform, and as a result, the voltage or current waveform does not become a sine wave such as that illustrated in FIG. 5 or 6, the abnormality in at least one of the average voltage value, average current value, impedance, frequency, phase difference, etc., can be expressed in the form of a numeric value, and can be distinguished from a normal value.

Further, by obtaining the average value from an n number of the most recent normal values, even when the effective values of the voltage and the current have fluctuated over time as a result of wear, or a rise in temperature, of the tool at the top end of the bonder, this average value becomes a determination criterion for determining whether or not the product is qualified to cope with such fluctuations.

The present invention has the following advantages.

(1) By high speed sampling of the data being performed using the DSP (Digital Signal Processor) and the data being digitized, it is possible to perform a post-processing of the data.

(2) Since the oscillation waveform data of the current and voltage is sampled, even past data regarding the frequency, phase difference, impedance and etc. is stored for each pin. By comparing this past data with an average value of a prescribed number of the most recent data, it is possible to detect bonding defects irrespective of differences in system types or the positions of the pins.

(3) Since of the oscillation waveforms are measured, it is possible to perform estimates on even a delicate bonding.

What is claimed is:

1. A bonding defect detecting apparatus for operation in conjunction with an ultrasonic wire bonder using an ultrasonic oscillator driven by a signal, comprising:

means for digitally converting at least one signal waveform of said signal to digital data by real-time sampling during a bonding operation;

digital signal processing means for calculating at least one signal characteristic of each of said at least one signal waveform from said digital data for each of a plurality of said bonding operation;

data accumulating means for accumulating said at least one signal characteristic for n number of bonding operations of said plurality of said bonding operation; and determining means for calculating an average signal characteristic of said at least one signal characteristics of said n number of bonding operations and comparing said average signal characteristic with a corresponding present signal characteristic of a last bonding operation of said plurality of said bonding operation, occurring after said n number of bonding operations, to thereby determine whether a bonding defect exists.

2. The bonding defect detecting apparatus as set forth in claim 1, wherein said n number of bonding operations are a most recent n number of bonding operations occurring before said last bonding operation.

3. The bonding defect detecting apparatus as set forth in claim 1, wherein said at least one signal characteristic represents a frequency of said at least one signal waveform.

4. The bonding defect detecting apparatus as set forth in claim 1, wherein:

said at least one signal waveform includes a voltage waveform and a current waveform; and said at least one signal characteristic represents one of a phase difference between said voltage waveform and a current waveform and an impedance determined from the voltage waveform and the current waveform.

5. A bonding defect detecting apparatus, for operating in conjunction with an ultrasonic wire bonder using an ultrasonic oscillator driven by a signal, wherein a plurality of product units are serially processed by the ultrasonic wire bonder and each of the product units has 1 through p number of bond positions upon each of which the ultrasonic wire bonder performs a bonding operation, the bonding defect detecting apparatus comprising:

means for digitally converting to digital data at least one signal waveform of said signal by real-time sampling for each of said bonding operations;

digital signal processing means for calculating from said digital data at least one signal characteristic of each of said at least one signal waveform for each of said bonding operations;

data accumulating means for accumulating said at least one signal characteristic for n number of said bonding operations for each of said bond positions for n number of said product units; and determining means for calculating an average signal characteristic of said at least one signal characteristic of said n number of said bonding operations for each of said bond positions and comparing said average signal characteristic with a corresponding present signal characteristic of a last bonding operation at a corresponding one of said bond positions, occurring after said n number of said bonding operations at said corresponding one of said bond positions, to thereby determine whether a bonding defect exists.

6. The bonding defect detecting apparatus as set forth in claim 5, wherein said n number of bonding operations are a most recent n number of said bonding operations at said corresponding one of said bond positions occurring before said last bonding operation.

7. The bonding defect detecting apparatus as set forth in claim 6, wherein said at least one signal characteristic represents a frequency of said at least one signal waveform.

8. The bonding defect detecting apparatus as set forth in claim 6, wherein:

said at least one signal waveform includes a voltage waveform and a current waveform; and said at least one signal characteristic represents one of a phase difference between said voltage waveform and said current waveform and an impedance determined from said voltage waveform and said current waveform.

9. The bonding defect detecting apparatus as set forth in claim 5, wherein said at least one signal characteristic represents a frequency of said at least one signal waveform.

10. The bonding defect detecting apparatus as set forth in claim 5, wherein:

said at least one signal waveform includes a voltage waveform and a current waveform; and said at least one signal characteristic represents one of a phase difference between said voltage waveform and said current waveform and an impedance determined from said voltage waveform and said current waveform.

11. The bonding defect detecting apparatus as set forth in claim 5, wherein said at least one signal characteristic is represented by X(N,P), where N designates a bonding operation number of one of said bonding operations and P designates a bond position of one of said 1 through p bond positions, said average signal characteristic for said bond position is represented by A(n, P) where $$A(n,P)=T(n,P)/n,$$

and $$T(n, P) = \sum_{N=1}^{n} X(N, P).$$

12. The bonding defect detecting apparatus as set forth claim 11, wherein m number of said bonding operations for each of said bond positions are conducted during serial processing of m number of said product units with said last bonding operation being designated by m, where m=n+1, said determining means effects said comparison of said average signal characteristic with said corresponding present signal characteristic in accordance with a defect comparison relationship $$A(m-1,P)-\alpha<X(m,P)<A(m-1,P)+\alpha,$$

wherein X(m,P) represents said corresponding present signal characteristic for bond position P, A(m-1,P) represents said average signal characteristic for said bond position P, and α represents a tolerance margin; and said determining means determines that said bonding defect exists when said defect comparison relationship is not satisfied.

13. The bonding defect detecting apparatus as set forth in claim 12, wherein said n number of bonding operations are a most recent n number of said bonding operations at said corresponding one of said bond positions occurring before said last bonding operation and, after said determining effects said comparison following said m number of said bonding operations, said determining means updates said average signal characteristic for said bond position P to a value A(m,P) in accordance with equations, $$A(m,P)=T(m,P)n,$$

and $$T(m,P)=T(m-1,P)-A(m-1,P)+X(m,P).$$

14. A bonding defect detecting method, comprising the steps of:

operating an ultrasonic wire bonder using an ultrasonic oscillator driven by a signal to perform bonding operations on m number of product units which are serially processed by the ultrasonic wire bonder and wherein performing said bonding operations includes performing a bonding operation on each of 1 through p bond positions of each of said product units;

digitally converting to digital data at least one signal waveform of said signal by real-time sampling for each of said bonding operations;

calculating from said digital data at least one signal characteristic of each of said at least one signal waveform for each of said bonding operations;

accumulating said at least one signal characteristic for n number of said bonding operations for each of said bond positions for n number of said product units;

calculating an average signal characteristic of said at least one signal characteristic of said n number of said bonding operations for each of said bond positions;

comparing said average signal characteristic with a corresponding present signal characteristic of a last bonding operation at a corresponding one of said bond positions, occurring after said n number of said bonding operations at said corresponding one of said bond positions; and determining whether a bonding defect exists based on an outcome of said step of comparing.

15. The bonding defect detecting method as set forth in claim 14, wherein said n number of bonding operations are a most recent n number of said bonding operations at said corresponding one of said bond positions occurring before said last bonding operation.

16. The bonding defect detecting method as set forth in claim 15, wherein said at least one signal characteristic represents a frequency of said at least one signal waveform.

17. The bonding defect detecting method as set forth in claim 15, wherein:

said at least one signal waveform includes a voltage waveform and a current waveform; and said at least one signal characteristic represents one of a phase difference between said voltage waveform and said current waveform and an impedance determined from said voltage waveform and said current waveform.

18. The bonding defect detecting method as set forth in claim 14, wherein said at least one signal characteristic represents a frequency of said at least one signal waveform.

19. The bonding defect detecting method as set forth in claim 14, wherein:

said at least one signal waveform includes a voltage waveform and a current waveform;

and said at least one signal characteristic represents one of a phase difference between said voltage waveform and said current waveform and an impedance determined from said voltage waveform and said current waveform.

20. The bonding defect detecting method as set forth in claim 14, wherein said at least one signal characteristic is represented by X(N,P), where N designates a bonding operation number of one of said bonding operations and P designates a bond position of one of said 1 through p bond positions, said average signal characteristic for said bond position is represented by A(n,P) and is calculated according to the equations, $$A(n,P)=T(n,P)/n,$$

and $$T(n, P) = \sum_{N=1}^{n} X(N, P).$$

21. The bonding defect detecting method as set forth in claim 20, wherein:

m number of said bonding operations for each of said bond positions are conducted during serial processing of said m number of said product units with said last bonding operation being designated by m, where m=n+1; and said step of comparing said average signal characteristic with said corresponding present signal determines whether a defect comparison relationship, $$A(m-1,P)-\alpha < X(m,P) < A(m-1,P)+\alpha, \text{ is satisfied}$$

wherein X(m,P) represents said corresponding present signal characteristic for bond position P, A(m−1,P) represents said average signal characteristic for said bond position P, and α represents a tolerance margin; and said step of determining whether a bonding defect exists includes determining that a bonding defect exists when said defect comparison relationship is not satisfied.

22. The bonding defect detecting method as set forth in claim 21, wherein said n number of bonding operations are a most recent n number of said bonding operations at said corresponding one of said bond positions occurring before said last bonding operation and, after said step of determining following said m number of said bonding operations, the method further comprises updating said average signal characteristic for said bond position P to a value A(m,P) in accordance with equations, $$A(m,P)=T(m,P)/n,$$

and $$T(m,P)=T(m-1,P)-A(m-1,P)+X(m,P).$$

23. A bond defect detecting apparatus for detecting defective bonds made on a workpiece, comprising;

means for effecting a bond on said workpiece using a transducer driven by a transducer signal;

means for digitizing said transducer signal and determining a signal characteristic of said transducer signal for each of said bond made on a plurality of said workpiece;

means for determining an average signal characteristic of said signal characteristics for said bond made on n number of said plurality of said workpiece after effecting said bond on an nth one of said plurality of said workpiece; and means for comparing said signal characteristic of said bond on an nth+1 one of said plurality of said workpiece with said average signal characteristic to determine whether said bond on said nth+1 one of said plurality of said workpiece is acceptable.

24. The bonding defect detecting apparatus as set forth in claim 23, wherein said n number of said plurality of said workpiece used in calculating said average signal characteristic exclude those determined to have a bonding defect.

25. The bonding defect detecting apparatus as set forth in claim 1, wherein said n number of bonding operations used in calculating said average signal characteristic exclude bonding operations determined to have produced a bonding defect.

26. The bonding defect detecting apparatus as set forth in claim 2, wherein said n number of bonding operations used in calculating said average signal characteristic exclude bonding operations determined to have produced a bonding defect.

27. The bonding defect detecting apparatus as set forth in claim 5, wherein said n number of bonding operations used in calculating said average signal characteristic exclude bonding operations determined to have produced a bonding defect.

28. The bonding defect detecting apparatus as set forth in claim 6, wherein said n number of bonding operations used in calculating said average signal characteristic exclude bonding operations determined to have produced a bonding defect.

29. The bonding defect detecting apparatus as set forth in claim 12, wherein said n number of bonding operations used in calculating said average signal characteristic exclude bonding operations determined to have produced a bonding defect.

30. The bonding defect detecting apparatus as set forth in claim 13, wherein said n number of bonding operations used in calculating said average signal characteristic exclude bonding operations determined to have produced a bonding defect.

31. The bonding defect detecting method as set forth in claim 14, wherein said n number of bonding operations used in calculating said average signal characteristic exclude bonding operations determined to have produced a bonding defect.

32. The bonding defect detecting method as set forth in claim 15, wherein said n number of bonding operations used in calculating said average signal characteristic exclude bonding operations determined to have produced a bonding defect.

33. The bonding defect detecting method as set forth in claim 21, wherein said n number of bonding operations used in calculating said average signal characteristic exclude bonding operations determined to have produced a bonding defect.

34. The bonding defect detecting method as set forth in claim 22, wherein said n number of bonding operations used in calculating said average signal characteristic exclude bonding operations determined to have produced a bonding defect.

\* \* \* \* \*